United States Patent [19]

Chakrabarti et al.

[11] Patent Number: 4,977,150
[45] Date of Patent: Dec. 11, 1990

[54] BENZODIAZEPINE COMPOUNDS AND THEIR USE AS PHARMACEUTICALS

[75] Inventors: Jiban Kumar Chakrabarti, Camberley; Terrence M. Hotten, Farnborough, both of England

[73] Assignee: Lilly Industries Limited, Basingstoke, England

[21] Appl. No.: 390,029

[22] Filed: Aug. 4, 1989

[30] Foreign Application Priority Data

Aug. 11, 1988 [GB] United Kingdom ............... 8819059

[51] Int. Cl.$^5$ .................... C07D 513/04; A61K 31/55
[52] U.S. Cl. .................................. 514/220; 510/557; 548/194
[58] Field of Search .................... 540/557; 514/220

[56] References Cited

U.S. PATENT DOCUMENTS

| | | | |
|---|---|---|---|
| 3,474,099 | 10/1969 | Renz et al. | 540/557 |
| 3,539,573 | 11/1970 | Schmutz et al. | 540/557 |
| 3,758,479 | 9/1973 | Schmutz et al. | 540/557 |
| 3,813,395 | 5/1974 | Nakanishi et al. | 540/557 |
| 3,951,981 | 4/1976 | Safir | 540/557 |
| 3,985,750 | 10/1976 | Protiva et al. | 540/557 |
| 4,115,568 | 9/1978 | Chakrabarti et al. | 540/557 |
| 4,115,574 | 9/1978 | Chakrabarti et al. | 540/557 |
| 4,404,137 | 9/1983 | Chakrabarti et al. | 540/557 |
| 4,431,589 | 2/1984 | Chakrabarti et al. | 540/557 |

OTHER PUBLICATIONS

S. Rajapa and R. Sreenivasan, *Indian J. Chem.*, 14B, Jun. 1976, pp. 394–396.

M. Sittig, *Pharmaceutical Manufacturing Encyclopedia*, 2nd ed., vol. 1, 1988, pp. 387–388.

*Primary Examiner*—Robert Gerstl
*Attorney, Agent, or Firm*—Joseph A. Jones; Leroy Whitaker

[57] ABSTRACT

Pharmaceutical thiazolo-[1,5]benzodiazepines of the formula

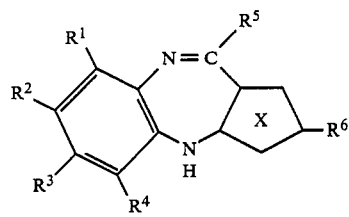

in which $R^1$, $R^2$, $R^3$ and $R^4$ are independently hydrogen, $C_{1-4}$ alkyl, $C_{2-4}$ alkenyl, halogen, $C_{1-4}$ haloalkyl, nitro, $C_{1-4}$ alkoxy, $C_{1-4}$ haloalkoxy, $C_{1-4}$ alkylthio or phenylsulphonyl; in which $R^5$ is a group of the formula

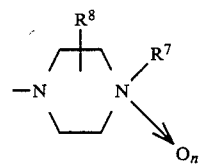

where $R^7$ is hydrogen, $C_{1-6}$ alkyl, $C_{3-7}$ cycloalkyl $C_{1-4}$ alkyl, benzyl or $ZO\text{-}C_{2-6}$ alkyl wherein Z is hydrogen or an acyl group, $R^8$ is hydrogen or $C_{1-4}$ alkyl and n is 0 or 1, provided that when $R^7$ is hydrogen n is 0; in which $R^6$ is hydrogen, $C_{1-10}$ alkyl, $C_{3-7}$ cycloalkyl, $C_{3-7}$ cycloalkyl $C_{1-4}$ alkyl, $C_{1-4}$ haloalkyl, $C_{1-4}$ alkoxy or $C_{1-4}$ alkylthio; and in which

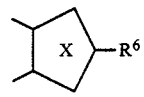

represents a thiazole ring selected from

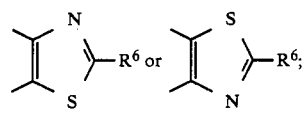

and acid addition salts thereof.

The compounds have cental nervous system activity.

7 Claims, No Drawings

BENZODIAZEPINE COMPOUNDS AND THEIR USE AS PHARMACEUTICALS

This invention relates to novel compounds, processes for preparing them and their use as pharmaceuticals.

Various tricyclic compounds with pharmaceutical properties have already been investigated, and for example British Patent No. 1 533 235 discloses some thieno-benzodiazepine compounds of this type. Such compounds are described as having useful activity on the central nervous system.

The compounds of the invention are thiazolo-[1,5]-benzodiazepines of the following formula

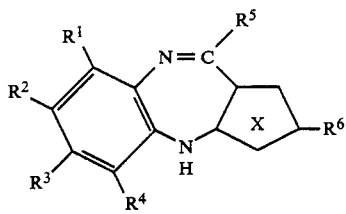
(I)

in which $R^1$, $R^2$, $R^3$ and $R^4$ are independently hydrogen, $C_{1-4}$ alkyl, $C_{2-4}$ alkenyl, halogen, $C_{1-4}$ haloalkyl, nitro, $C_{1-4}$ alkoxy, $C_{1-4}$ haloalkoxy, $C_{1-4}$ alkylthio or phenylsulphonyl; in which $R^5$ is a group of the formula

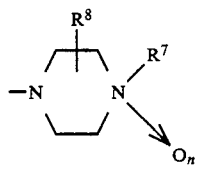

where $R^7$ is hydrogen, $C_{1-6}$ alkyl, $C_{3-7}$ cycloalkyl $C_{1-4}$ alkyl, benzyl or $ZO-C_{2-6}$ alkyl where Z is hydrogen or an acyl group, $R^8$ is hydrogen or $C_{1-4}$ alkyl and n is 0 or 1, provided that when $R^7$ is hydrogen n is 0; in which $R^6$ is hydrogen, $C_{1-10}$ alkyl, $C_{3-7}$ cycloalkyl, $C_{3-7}$ cycloalkyl $C_{1-4}$ alkyl, $C_{1-4}$ haloalkyl, $C_{1-4}$ alkoxy or $C_{1-4}$ alkylthio; and in which

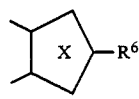

represents a thiazole ring selected from

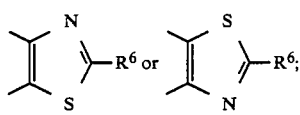

and acid addition salts thereof.

Compounds of formula (I) have been found to possess useful biological properties and the invention includes a compound of formula (I) for use as a pharmaceutical, especially for use in treating disorders of the central nervous system.

A preferred group of compounds of formula (I) is one in which $R^1$, $R^2$, $R^3$ and $R^4$ independently represent hydrogen, halogen or $C_{1-4}$ haloalkyl, $R^6$ is hydrogen, $C_{1-6}$ alkyl, $C_{3-7}$ cycloalkyl, $C_{3-7}$ cycloalkyl $C_{1-4}$ alkyl or $C_{1-4}$ alkylthio, $R^7$ is hydrogen or $C_{1-4}$ alkyl, $R^8$ is hydrogen and n is 0, being of the formula:

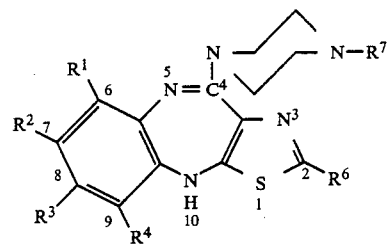

and acid addition salts thereof.

In the above general formula (I), the term "$C_{1-10}$ alkyl" means a straight or branched chain alkyl group containing 1 to 10 carbon atoms and is especially "$C_{1-6}$ alkyl", for example, methyl, ethyl, isopropyl, propyl, butyl, sec. butyl, isobutyl, tert. butyl, pentyl or hexyl. A preferred alkyl group is "$C_{1-4}$ alkyl". The term "$C_{1-4}$ haloalkyl" means any such alkyl group substituted by one or more, preferably three halogen atoms, and is especially trifluoromethyl. The term "halogen" is preferably bromine, fluorine and chlorine, and especially chlorine and fluorine. The terms "$C_{1-4}$ alkoxy" and "$C_{1-4}$ alkylthio" mean any $C_{1-4}$ alkyl group attached through an oxygen or sulphur atom to a ring atom and "$C_{1-4}$ haloalkoxy" means a $C_{1-4}$ alkoxy group substituted by one or more, preferably three halogen atoms and is especially trifluoromethoxy. The term "$C_{2-4}$ alkenyl" refers to groups such as vinyl, allyl and butenyl. "$C_{3-7}$ Cycloalkyl" means a saturated ring having 3 to 7 carbon atoms in the ring such as cyclopropyl, cyclobutyl, cyclopentyl, cyclohexyl or cycloheptyl, which can, in the group "$C_{3-7}$ cycloalkyl $C_{1-4}$ alkyl", be attached to the ring via an alkyl chain having 1 to 4 carbon atoms.

When $R^7$ is $ZO-C_{2-6}$ alkyl, Z is hydrogen or an acyl group. Preferably when Z is an acyl group, the group is of the formula RCO- where R is $C_{1-20}$ alkyl, for example, $C_{10-12}$ alkyl. Preferred examples of $R^7$ of this type are hydroxyethyl or hydroxypropyl of the formula -$(CH_2)_m$OH where m is 2 or 3.

The $R^6$ and $R^7$ groups are preferably $C_{1-4}$ alkyl, for example methyl or ethyl. Preferably also $R^1$, $R^4$ and $R^8$ are hydrogen, and n is 0, and X is

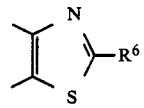

A particular group of compounds is one of the following formula

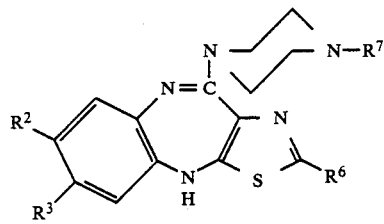

in which $R^2$ and $R^3$ independently represent hydrogen or halogen, $R^6$ is $C_{1-4}$ alkyl and $R^7$ is $C_{1-4}$ alkyl.

Examples of the compounds of the invention are as follows:
8-Fluoro-2-methyl-4-(4-methyl-1-piperazinyl)-10H-thiazolo[5,4-b][1,5]benzodiazepine
2-Methyl-4-(4-methyl-1-piperazinyl)-10H-thiazolo[5,4-b][1,5]benzodiazepine
7-Fluoro-2-methyl-4-(4-methyl-1-piperazinyl)-10H-thiazolo[5,4-b][1,5]benzodiazepine
7-Chloro-2-methyl-4-(4-methyl-1-piperazinyl)-10H-thiazolo[5,4-b][1,5]benzodiazepine
7,8-Difluoro-2-methyl-4-(4-methyl-1-piperazinyl)-10H-thiazolo-[5,4-b][1,5]benzodiazepine
2-Ethyl-4-(4-methyl-1-piperazinyl)-10H-thiazolo[5,4-b][1,5]benzodiazepine
2-Ethyl-8-fluoro-4-(4-methyl-1-piperazinyl)-10H-thiazolo[5,4-b][1,5]benzodiazepine
2-Ethyl-7-fluoro-4-(4-methyl-1-piperazinyl)-10H-thiazolo[5,4-b][1,5]benzodiazepine
7-Chloro-2-ethyl-4-(4-methyl-1-piperazinyl)-10H-thiazolo[5,4-b][1,5]benzodiazepine
4-(8-Fluoro-2-methyl-10H-thiazolo[5,4-b][1,5]benzodiazepin-4-yl)-1-methyl piperazine-1-oxide
4-(2-Methyl-10H-thiazolo[5,4-b][1,5]benzodiazepin-4-yl)-1-methyl piperazine-1-oxide
4-(7-Fluoro-2-methyl-10H-thiazolo[5,4-b][1,5]benzodiazepin-4-yl)-1-methyl piperazine-1-oxide
4-(7-Fluoro-2-methyl-10H-thiazolo[5,4-b][1,5]benzodiazepin-4-yl)-piperazine-1-ethanol
4-(7-Chloro-2-methyl-10H-thiazolo[5,4-b][1,5]benzodiazepin-4-yl)-1-methyl piperazine-1-oxide
8-Fluoro-2-methyl-10-(4-methyl-1-piperazinyl)-4H-thiazolo[4,5-b][1,5]benzodiazepine
2-Methyl-10-(4-methyl-1-piperazinyl)-4H-thiazolo[4,5-b][1,5]benzodiazepine
7-Fluoro-2-methyl-10-(4-methyl-1-piperazinyl)-4H-thiazolo[4,5-b][1,5]benzodiazepine
7-Chloro-2-methyl-10-(4-methyl-1-piperazinyl)-4H-thiazolo[4,5-b][1,5]benzodiazepine;
and acid addition salts thereof.

As indicated above, the compounds of the invention are useful both in their free base and acid addition salt forms. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric or lactic acid, or organic sulphonic acids for example methane sulphonic, ethane sulphonic, 2-hydroxyethane sulphonic, toluene-p-sulphonic or naphthalene-2-sulphonic acid. Apart from pharmaceutically acceptable acid addition salts, other salts are also included within the scope of acid addition salts such as, for example, those with picric or oxalic acid, since they may serve as intermediates in the purification of the compounds or in the preparation of other, for example, pharmaceutically acceptable, acid addition salts, or are useful for identification, characterization or purification of the bases.

According to a further aspect of the invention there is provided a process for producing a compound of formula (I) or an acid addition salt thereof, which comprises (a) ring-closing a compound of formula (II)

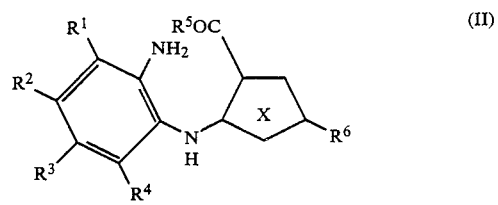

in which $R^1$ to $R^6$ and X have the values defined above, optionally followed when $R^7$ is hydrogen by alkylation to give a compound in which $R^7$ is $C_{1-6}$ alkyl, $C_{3-7}$ cycloalkyl $C_{1-4}$ alkyl, benzyl or $ZO\text{-}C_{2-6}$ alkyl where Z is hydrogen or an acyl group, (b) reacting an amine of formula $R^5H$ with a compound of formula (III)

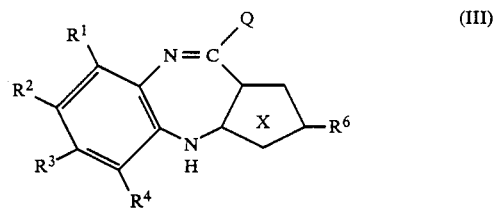

in which $R^1$ to $R^6$ and X have the values defined above and Q represents a radical capable of being split off with the hydrogen atom of the amine $R^5H$, optionally followed when $R^7$ is hydrogen by alkylation to give a compound in which $R^7$ is $C_{1-6}$ alkyl, $C_{3-7}$ cycloalkyl $C_{1-4}$ alkyl, benzyl or $ZO\text{-}C_{2-6}$ alkyl where Z is hydrogen or an acyl group, or (c) oxidising a compound of formula (I) in which $R^7$ is $C_{1-6}$ alkyl, $C_{3-7}$ cycloalkyl $C_{1-4}$ alkyl, benzyl or $ZO\text{-}C_{2-6}$ alkyl where Z is an acyl group and n is 0, to give a compound in which n is 1.

The above processes are of a general type previously described in the literature and appropriate reaction conditions, and suitable Q radicals can be readily chosen.

In reaction (a), compounds of formula (II) may be ring-closed by employing, for example, as catalyst titanium tetrachloride and as solvent anisole, and preferably at a temperature of 100° C. to 250° C., for example from 150° C. to 200° C. The compounds of formula (II) are preferably prepared in situ without isolation, as described below.

It may be mentioned, for example, that in reaction (b) the radical Q can be an amino group or a mono- or dialkyl-substituted amino group (each alkyl substituent containing 1 to 4 carbon atoms), hydroxyl, thiol, or an alkoxy, alkylthio or alkylsulphonyl group containing 1 to 4 carbon atoms, for example a methoxy or methylthio group, or a halogen atom, especially a chlorine atom. Preferably, Q is amino ($NH_2$), hydroxyl or thiol, and amino is most preferred. The reaction is preferably carried out at a temperature of from 50° C. to 200° C.

When Q is amino the intermediates of formula (III) may also exist in the imino form:

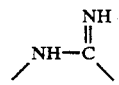

and when Q is hydroxyl or thiol, the intermediates of formula (III) may exist in their amide and thioamide forms:

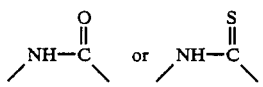

The amidines of formula (III) (Q is NH$_2$), can be in a salt form for example as the hydrochloride, and they can be reacted with amines of formula R$^5$H, optionally diluted with a solvent such as anisole, toluene, dimethylformamide or dimethylsulphoxide, and at a temperature range of 100° to 150° C. Alternatively the amidine can be converted into the corresponding amide of formula (III) (Q is OH) by alkaline hydrolysis.

When Q is hydroxyl, reaction (b) can be accomplished in the presence of titanium tetrachloride which has the ability to react with the amine of formula R$^5$H to form a metal amine complex. Other metal chlorides such as those of zirconium, hafnium or vanadium may also be employed. The reaction can be carried out in the presence of an acid binding agent such as a tertiary amine, for example, triethylamine.

Alternatively, the reaction can be carried out using excess of the amine of formula R$^5$H to act as an acid-binding agent. A suitable organic solvent such as toluene or chlorobenzene can be used as a reaction medium, although it has been found that the use of anisole is particularly desirable, at least as a co-solvent, in view of its ability to form a soluble complex with TiCl$_4$.

If desired, elevated temperatures, for example up to 200° C., can be used to expedite the reaction and a preferred temperature range for carrying out the reaction is from 80° C. to 120° C.

Thioamides of formula (III) (Q is SH), iminothioethers, iminoethers or iminohalides, or other derivatives containing active Q radicals as specified above, tend to be more reactive towards the amine R$^5$H and can usually be reacted without the necessity for the presence of TiCl$_4$, but otherwise employing the same conditions of temperature and solvent.

When it is desired to prepare a compound in which R$^7$ is other than hydrogen, it is preferred to start with the reactants of formula (II) or amine of formula R$^5$H, in which R$^7$ has the required value, and then to perform reaction (a) or (b). However, as an alternative, the corresponding compound of formula (I) in which R$^7$ is hydrogen may first be prepared and this then reacted with a suitable alkylating agent of formula R$^7$X by conventional methods employing an inert solvent and base, X being a leaving group such as for example chlorine, bromine or iodine, or a group such as tosyl or mesyl.

As mentioned above, in reaction (c), compounds of formula (I) in which R$^7$ is other than hydrogen and n is 1, can be made by oxidation of the corresponding compounds in which n is 0. Suitable oxidising agents include for example m-chloroperbenzoic acid and the reaction is preferably carried out in an inert solvent such as for example dichloromethane, at a temperature of from −20° C. to +20° C. for example from −10° C. to +10° C.

The compounds of formula (I) produced by the above processes may be isolated per se or may be converted to their corresponding acid addition salts using conventional methods.

Intermediate compounds of formula (II) in process (a) described above, are preferably prepared in situ without isolation by reacting a compound of formula

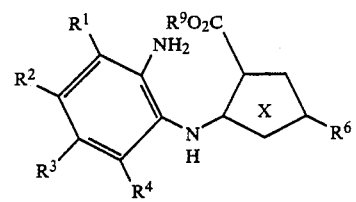

in which R$^1$ to R$^4$ and R$^6$ have the values defined above and R$^9$ is an ester group, preferably C$_{1-4}$ alkyl, with an amine of formula R$^5$H, such as by heating to a temperature between 30° C. and 120° C., for example about 100° C., in a suitable solvent such as for example anisole, and employing TiCl$_4$ as catalyst.

Compounds of formula (IV) can be prepared from the corresponding nitro compounds of formula

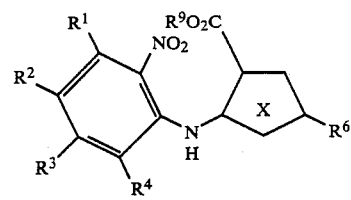

if convenient, without isolation, for directly reacting with amine R$^5$H. Intermediate compounds of formula (V) are novel
and are included as an aspect of the present invention. They can be made by condensation of a thiazole compound of formula

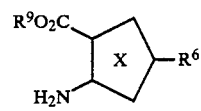

with an ortho-halonitrobenzene of formula

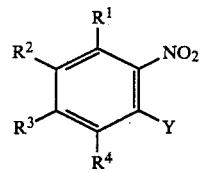

where Y is a halogen, preferably fluorine, bromine or chlorine, in the presence of a base for example, sodium hydride, in a solvent such as for example tetrahydrofuran and at a temperature of from −20° C. to 30° C., or anhydrous potassium carbonate in a solvent such as dimethylsulphoxide at a temperature of from 90° C. to 120° C. Compounds of formula (V) are converted to the compounds of formula (IV) by reduction, for example catalytically, employing for instance, hydrogen and palladium/carbon or chemically, employing for example, stannous chloride and hydrogen chloride in aqueous ethanol, or ammonium polysulphide.

An illustration of the preparation of representative compounds of the invention (4-(4-alkyl-1-piperazinyl)-

10H-thiazolo[5,4-b][1,5]benzodiazepines) by this route is given in the reaction scheme below:

from the esters of formula (IV) by basic hydrolysis using for example sodium hydroxide in ethanol.

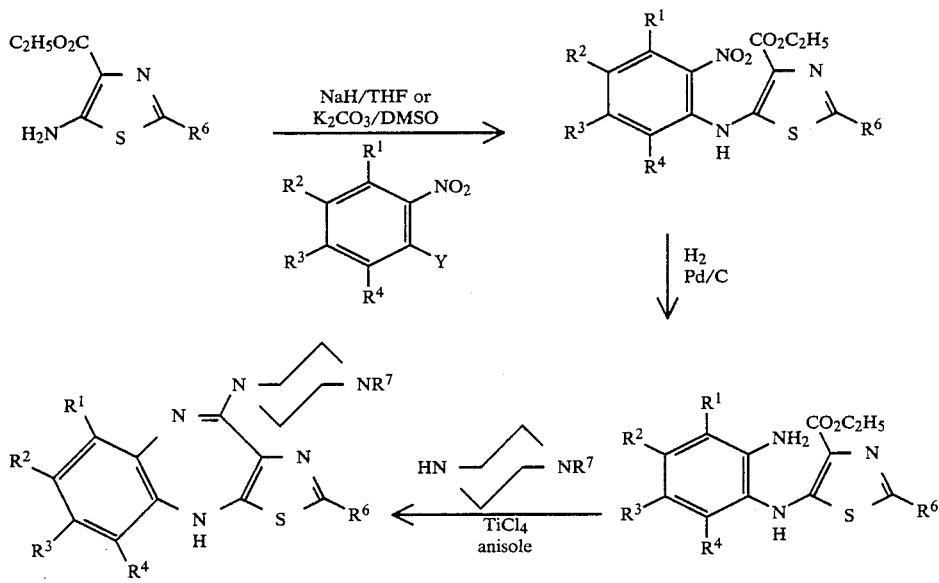

The intermediate amidines of formula (III) (Q is NH$_2$), employed in process (b), can be prepared by condensation of a thiazole of formula

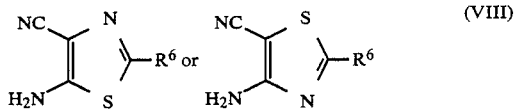

with an ortho-halonitrobenzene of formula (VII) above, in the presence of a base for example, sodium hydride in a solvent such as tetrahydrofuran or n-butyl lithium in tetrahydrofuran, or potassium carbonate in dimethylsulphoxide or with a tetraalkylammonium salt in a two-phase system, to form a nitronitrile of formula:

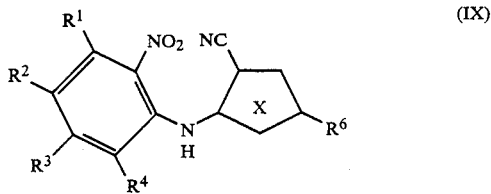

which can he simultaneously reduced and ring-closed to the amidine of formula (III) employing for example, stannous chloride and hydrogen chloride in aqueous ethanol or, alternatively by reduction with hydrogen and palladium/carbon or ammonium polysulphide followed by acid-catalysed ring closure.

Similarly, the intermediates amides of formula (III) (Q is OH), employed in process (b), can be derived from compounds of formula (IV) above, by ring closure employing for example sodium methylsulphinyl methanide in a suitable solvent such as dimethylsulphoxide can give an amide of formula (III) (Q is OH). Alternatively, these amides can be prepared by ring closure of an amino-acid, employing for example dicyclohexylcarbodiimide (DCC) in a suitable solvent such as tetrahydrofuran. These amino-acids can be obtained for example Thioamides of formula (III) (Q is SH) can be prepared by treating a solution of the corresponding amide in an anhydrous basic solvent such as for example pyridine with phosphorus pentasulphide. Similarly, the amides can be converted to iminothioethers, iminoethers or iminohalides, or other derivatives containing active Q radicals, by treatment with conventional reagents such as for example in the case of an iminochloride, phosphorus pentachloride.

Thiazole starting materials of formulae (VI) and (IX), used in the processes described above, are either known compounds, see for example Chem. & Ind. (1970) 1470; J.Chem.Soc. (1947) 1594, 1598; (1948) 2028; (1959) 4040; J.Prakt.Chem. (1967) 35 70; Arch.Pharm. (Weinheim) (1970) 303 625; Tetrahedron Lett. (1981) 22 2285; Monatsch.Chem. (1981) 112 1393; Bull.Chem.Soc. Japan (1983) 56 3851; J.Prakt. Chem. (1985) 327 604; Liebigs Ann.Chem. (1986) 780; or can be prepared by conventional techniques from known compounds. The ortho-halonitrobenzene intermediates are either commercially available or can be simply prepared from commercially available substances.

As mentioned above, the compounds of the invention have useful central nervous system activity. This activity has been demonstrated in animal models using well-established procedures. In behavioural studies in mice, for instance, the compounds of the invention described in the following Examples were observed to produce activity decrease at a dose range of 1.6 to 200 mg/kg p.o. In addition compounds have been found to be active in the spiroperidol binding test described by P. Seeman et al., in Nature 261, 717–719 (1976) and for example have an IC$_{50}$ value (the concentration of the compound required to reduce the binding of spiroperidol by 50 per cent) of less than 1 $\mu$M. Thus the compounds are potent centrally acting agents with neuroleptic, sedative or relaxant, anxiolytic or anti-emetic properties. These properties, coupled with their high therapeutic index, render them useful in the treatment of certain kinds of psychotic conditions such as schizophrenia and acute mania and of mild anxiety states.

The compounds of this invention are effective over a wide dosage range, the actual dose administered being dependent on such factors as the particular compound being used, the condition being treated and the type and size of mammal being treated. However, the dosage required will normally fall within the range of 0.01 to 2 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula I or a pharmaceutically acceptable acid addition salt thereof, associated with a pharmaceutically acceptable carrier. In making the compositions of the invention, the active ingredient will usually be mixed with a carrier or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions for parenteral use or as suppositories. A preferred formulation is an injection especially a sustained release formulation for intramuscular injection. Preferably the compositions are formulated in a dosage unit form, each dosage containing from 0.5 to 100 mg, more usually 1 to 100 mg, of the active ingredient.

The following Examples illustrate the invention:

EXAMPLE 1

Ethyl 5-(5-fluoro-2-nitrophenylamino)-2-methylthiazole-4-carboxylate

Ethyl 5-amino-2-methylthiazole-4-carboxylate (Chem.& Ind. (1970) 1470) (3.72 g) 2,4-difluoronitrobenzene (3.2 g) and potassium carbonate (5.6 g) were stirred under a nitrogen atmosphere in dimethylsulphoxide (80 ml) at 110° C. for 50 minutes. The mixture was poured onto a mixture of crushed ice and 2M hydrochloric acid (100 ml) and extracted into dichloromethane. The extract was washed with water, dried with magnesium sulphate and the solvent removed to leave the product, which was purified by chromatography on a column of silica and recrystallisation from ethanol, m.p. 179°–182° C.

Similarly prepared were:

Ethyl 5-(4-fluoro-2-nitrophenylamino)-2-methylthiazole-4-carboxylate, m.p. 170°–174° C.

Ethyl 5-(4-chloro-2-nitrophenylamino)-2-methylthiazole-4-carboxylate, m.p. 175°–181° C.

Ethyl 5-(2-nitrophenylamino)-2-methylthiazole-4-carboxylate, m.p. 133°–134° C.

EXAMPLE 2

Ethyl 5-(2-nitrophenylamino)-2-methylthiazole-4-carboxylate

To sodium hydride (50% oil dispersion, 1.44 g) in dry tetrahydrofuran (25 ml) under a nitrogen atmosphere was added ethyl 5-amino-2-methylthiazole-4-carboxylate (2.78 g) and o-fluoronitrobenzene (2.82 g) in tetrahydrofuran (100 ml). The mixture was stirred at 25° C. for 20 hours and carefully poured onto excess crushed ice. The mixture was acidified with 2M hydrochloric acid and the precipitate filtered, washed with water and dried. The crude product was recrystallised from ethanol, m.p. 133°–134° C.

Ethyl 5-(4-fluoro-2-nitrophenylamino)-2-methylthiazole-4-carboxylate, m.p. 170°–174° C., was similarly prepared.

EXAMPLE 3

8-Fluoro-2-methyl-4-(4-methyl-1-piperazinyl)-10H-thiazolo [5,4-b]-[1,5]benzodiazepine Ethyl 5-(5-fluoro-2-nitrophenylamino)-2-methylthiazole-4-carboxylate (2.85 g) was hydrogenated at 60 p.s.i. in ethanol (100 ml) with 10% palladium on charcoal (0.35 g). The catalyst was removed by filtration and the solvent removed under reduced pressure to leave the diaminoester which was used without further purification in the next stage.

This diaminoester was stirred in a mixture of N-methylpiperazine (17.65 ml) and anisole (40 ml) under a nitrogen atmosphere. A solution of titanium tetrachloride (2.9 ml) in anisole (15 ml) was added over 5 minutes and the stirred mixture heated at 100° C. for 1 hour and then at 160°–180° C., under reflux, for 48 hours. After cooling the stirred mixture to about 70° C., a mixture of 20M ammonia solution (5 ml) and 2-propanol (5 ml) was cautiously added. The stirred suspension was allowed to slowly cool to 25° C. over 1 hour to precipitate the titanium salts which were then removed by filtration through a pad of celite, washing with ethyl acetate (100 ml). The combined filtrate and washings were extracted twice with 2N hydrochloric acid and the extracts washed with ethyl acetate. The acid solution was basified with 20M ammonia solution and extracted into dichloromethane. After washing with water and drying with magnesium sulphate the solvent was removed under reduced pressure to leave the crude product which was purified by chromatography on a column of magnesium silicate followed by crystallisation from acetonitrile, m.p. 234°–237° C.

Similarly prepared were:

2-Methyl-4-(4-methyl-1-piperazinyl)-10H-thiazolo[5,4-b][1,5]benzodiazepine, m.p. 258°–263° C. (acetonitrile)

7-Fluoro-2-methyl-4-(4-methyl-1-piperazinyl)-10H-thiazolo-[5,4-b][1,5]benzodiazepine, m.p. 253°–255° C. (acetonitrile)

7-Chloro-2-methyl-4-(4-methyl-1-piperazinyl)-10H-thiazolo-[5,4-b][1,5-benzodiazepine, m.p. 256°–264° C. (acetonitrile)

EXAMPLE 4

Tablets each containing 10 mg of active ingredient are made up as follows

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the Sranules which, after mixing, are compressed on a tablet machine to yield tablets each weighing 300 mg.

EXAMPLE 5

Capsules each containing 20 mg of medicament are made as follows

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

EXAMPLE 6

A freeze dried formulation for reconstitution into an aqueous injection is prepared from the following ingredients

| | |
|---|---|
| Active ingredient | 15 mg |
| 0.1M Hydrochloric acid | 0.48 ml |
| Mannitol | 100 mg |
| Water | to 2 ml |

The active ingredient is suspended in water, acidified with hydrochloric acid and mannitol added, and adjusted to pH5. Water is added to 2 ml and the mixture filled into vials and then freeze dried.

EXAMPLE 7

A sustained release formulation for intra-muscular injection is prepared from the following ingredients

| | |
|---|---|
| Active ingredient | 20 mg |
| Aluminium stearate | 2 mg |
| Soya bean oil | to 2 ml |

We claim:
1. A compound of the formula

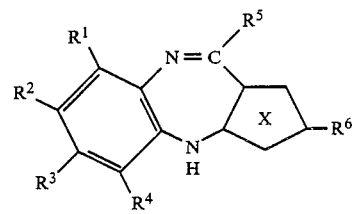

in which $R^1$, $R^2$, $R^3$ and $R^4$ are independently hydrogen, $C_{1-4}$ alkyl, $C_{2-4}$ alkenyl, halogen, $C_{1-4}$ haloalkyl, nitro, $C_{1-4}$ alkoxy, $C_{1-4}$ haloalkoxy, $C_{1-4}$ alkylthio or phenylsulphonyl; in which $R^5$ is a group of the formula

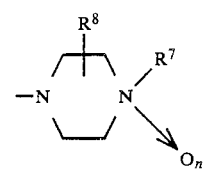

where $R^7$ is hydrogen or $C_{1-6}$ alkyl, $C_{3-7}$ cycloalkyl $C_{1-4}$ alkyl or benzyl or $ZO-C_{2-6}$ alkyl where Z is hydrogen $C_{1-20}$ acyl group, $R^8$ is hydrogen or $C_{1-4}$ alkyl and n is 0 or 1, provided that when $R^7$ is hydrogen n is 0; in which $R^6$ is hydrogen, $C_{1-10}$ alkyl, $C_{3-7}$ cycloalkyl, $C_{3-7}$ cycloalkyl $C_{1-4}$ alkyl, $C_{1-4}$ haloalkyl, $C_{1-4}$ alkoxy or $C_{1-4}$ alkylthio; and in which

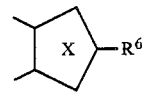

represents a thiazole ring selected from

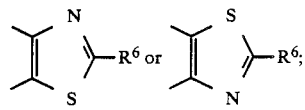

and acid addition salts thereof.

2. A compound according to claim 1 in which the thiazole ring is

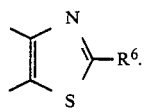

3. A compound according to claim 1 in which the thiazole ring is

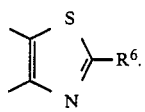

4. A compound of the formula

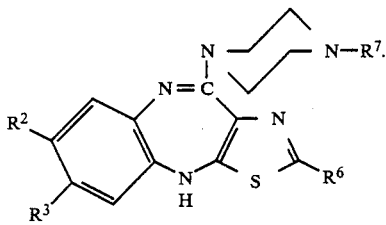

in which $R^1$, $R^2$, $R^3$ and $R^4$ independently represent hydrogen, halogen or $C_{1-4}$ haloalkyl, $R^6$ is hydrogen, $C_{1-6}$ alkyl, $C_{3-7}$ cycloalkyl, $C_{3-7}$ cycloalkyl $C_{1-4}$ alkyl or $C_{1-4}$ alkylthio, $R^7$ is hydrogen or $C_{1-4}$ alkyl; and acid addition salts thereof.

5. A compound according to claim 4 in which $R^1$ and $R^4$ are hydrogen and $R^2$ and $R^3$ are independently hydrogen or halogen, $R^6$ is $C_{1-4}$ alkyl and $R^7$ is $C_{1-4}$ alkyl.

6. A pharmaceutical formulation comprising an effective amount of a compound according to any of claims 1 to 5, or a pharmaceutically acceptable acid addition salt thereof, together with a pharmaceutically acceptable diluent or carrier therefor.

7. A method of treating an animal, including a human, suffering from or susceptible to a disorder of the central nervous system, which comprises administering an effective amount of compound as defined in claim 1, or a pharmaceutically-acceptable salt thereof.

* * * * *

UNITED STATES PATENT AND TRADEMARK OFFICE
CERTIFICATE OF CORRECTION

PATENT NO. : 4,977,150

DATED : December 11, 1990

INVENTOR(S) : Jiban K. Chakrabarti et al

It is certified that error appears in the above-identified patent and that said Letters Patent is hereby corrected as shown below:

Column 12, line 27 and 28, the phrase "hydrogen $C_{1-20}$" should read -- hydrogen or a $C_{1-20}$ --.

Column 13, line 13, the phrase "$R^1$, $R^2$, $R^3$ and $R^4$" should read -- $R^2$ and $R^3$ --.

Column 14, lines 3 and 4, the phrase "$R^1$ and $R^4$ are hydrogen and" should be deleted.

Signed and Sealed this

Twenty-fourth Day of November, 1992

Attest:

DOUGLAS B. COMER

Attesting Officer

Acting Commissioner of Patents and Trademarks